(12) United States Patent
Boday et al.

(10) Patent No.: US 9,700,635 B2
(45) Date of Patent: Jul. 11, 2017

(54) HYDROGELS FROM DYNAMIC COVALENT NETWORKS

(71) Applicant: International Business Machines Corporation, Armonk, NY (US)

(72) Inventors: Dylan J. Boday, Tucson, AZ (US); Mareva B. Fevre, San Jose, CA (US); Jeannette M. Garcia, San Leandro, CA (US); James L. Hedrick, Pleasanton, CA (US); Rudy J. Wojtecki, San Jose, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 14/938,577

(22) Filed: Nov. 11, 2015

(65) Prior Publication Data

US 2017/0128590 A1    May 11, 2017

(51) Int. Cl.
| | | |
|---|---|---|
| *C08G 73/06* | (2006.01) | |
| *A61K 47/48* | (2006.01) | |
| *C08G 65/333* | (2006.01) | |
| *C08G 75/04* | (2016.01) | |
| *C08G 81/00* | (2006.01) | |
| *C09D 179/06* | (2006.01) | |
| *C08L 79/04* | (2006.01) | |
| *C08K 5/3492* | (2006.01) | |

(52) U.S. Cl.
CPC .. *A61K 47/48784* (2013.01); *A61K 47/48192* (2013.01); *A61K 47/48215* (2013.01); *C08G 65/33317* (2013.01); *C08G 73/0644* (2013.01); *C08G 75/04* (2013.01); *C08G 81/00* (2013.01); *C08K 5/3492* (2013.01); *C08L 79/04* (2013.01); *C09D 179/06* (2013.01)

(58) Field of Classification Search
CPC .............. C08G 73/0644; C09D 179/06; C09D 181/02; C08F 8/28; C10L 2230/14; C10L 2290/542; C10L 2290/547; C10L 3/103; C08L 79/04; C08K 5/3492; C08J 2379/04
See application file for complete search history.

(56) References Cited

U.S. PATENT DOCUMENTS 2,838,466 A * 6/1958 Padbury ................ C09K 17/20
106/287.2
7,129,293 B2   10/2006 Kataoka et al.

FOREIGN PATENT DOCUMENTS

| CN | 102702460 A | 10/2012 |
|---|---|---|
| CN | 103450434 A | 12/2013 |
| CN | 103834157 A | 6/2014 |
| EP | 0158394 A1 | 10/1985 |

OTHER PUBLICATIONS

Hiller et al (Laser-engravable hexahydrotriazine polymer network, Mat Res Innovat (2002) 6:179-184), Jan. 2002.*
Wojtecki et al (Developments in Dynamic Covalent Chemistries from the Reaction of Thiols with Hexahydrotriazines, J. Am. Chem. Soc. 2015, 137, 14248-14251), published Oct. 27, 2015.*

* cited by examiner

*Primary Examiner* — Gregory Listvoyb
(74) *Attorney, Agent, or Firm* — Patterson + Sheridan, LLP

(57) ABSTRACT

A polymer is described herein that includes a plurality of N-J-N or N—C—S repeating units, wherein each J is independently a carbon atom, an alkyl group, or an aryl group; a plurality of hydrophilic groups bonded with the repeating units; and a plurality of hydrophobic groups bonded with the hydrophilic groups and the repeating units. Such polymers may be made into hydrogels by exposure to water, and the hydrogels may be used as delivery vehicles for various payloads.

4 Claims, 2 Drawing Sheets

HYDROGELS FROM DYNAMIC COVALENT NETWORKS

FIELD

The present invention relates to methods of making hydrogel polymers and uses thereof.

BACKGROUND

Hydrogels are a class of materials formed from natural or synthetic polymers that exhibit three-dimensional (3D) networks with high to ultra-high degree of water content. While the term has been used as early as 1894, the first biological use of such gels was only reported by Wichterle and Lim in 1960. Since then, there has been an explosion of investigations documenting the use of hydrogels in many biomedical applications, including medicine and protein delivery, tissue engineering, cell culture, coatings and wound dressing. The methodologies involving the production of such materials have also seen substantial increase in recent years especially with regards to the type of physical and chemical cross-linking processes.

Hydrogels produced from the self-assembly of synthetic polymers have an inexhaustible potential to serve as delivery matrix for localized administration of theranostic components. Recent developments in polymer chemistry have enabled polymers to be synthesized with well-controlled composition and architecture. Highly versatile orthogonal functionalization strategies also allow gelation of such polymers and containment of payload through one or a combination of the following association mechanisms such as hydrophobic interactions, ionic interactions, hydrogen bonding, physical entanglement of macromolecules and chemical cross-linking of the matrix. A number of physical gel systems have been formulated using the 'ABA'-type triblock copolymers and the polymeric amphiphiles can be designed with either the 'A' or 'B' constituent blocks to be hydrophilic or hydrophobic. Many of such systems engages the use of poly(ethylene glycol) (PEG) as the uncharged hydrophilic constituent block due to its biocompatibility. Some commonly used hydrophobic components include biodegradable poly(L-lactic acid) (PLLA), poly(L-glycolic acid), poly(lactic-co-glycolic acid) (PLGA) and poly(caprolactone). They can either form the middle 'B' block (e.g. PEG-PLGA-PEG) or as the terminus 'A' blocks (e.g. PLLA-PEG-PLLA). Aqueous mixture of enantiomeric triblock copolymers (e.g. PLLA-PEG-PLLA and PDLA-PEG-PDLA) could also form physical gels via stereocomplexation. Most 'ABA'-type polymers require high concentration and/or hydrophobic content for hydrogel formation. For instance, PLLA-b-PEG-b-PLLA containing high lactide content of 17 to 37 wt. % require a minimum concentration of 16 wt. % for gelation. Such high hydrophobic compositions can give rise to adverse physiological effects during in vivo degradation. Thus, it is desirable to develop biodegradable polymeric materials that can form hydrogels at a low concentration.

SUMMARY

A polymer is described herein that includes a plurality of N-J-N or N—C—S repeating units, wherein each J is independently a carbon atom, an alkyl group, or an aryl group; a plurality of hydrophilic groups bonded with the repeating units; and a plurality of hydrophobic groups bonded with the hydrophilic groups and the repeating units. Such polymers may be made into hydrogels by exposure to water, and the hydrogels may be used as delivery vehicles for various payloads.

DETAILED DESCRIPTION

Figure 1:
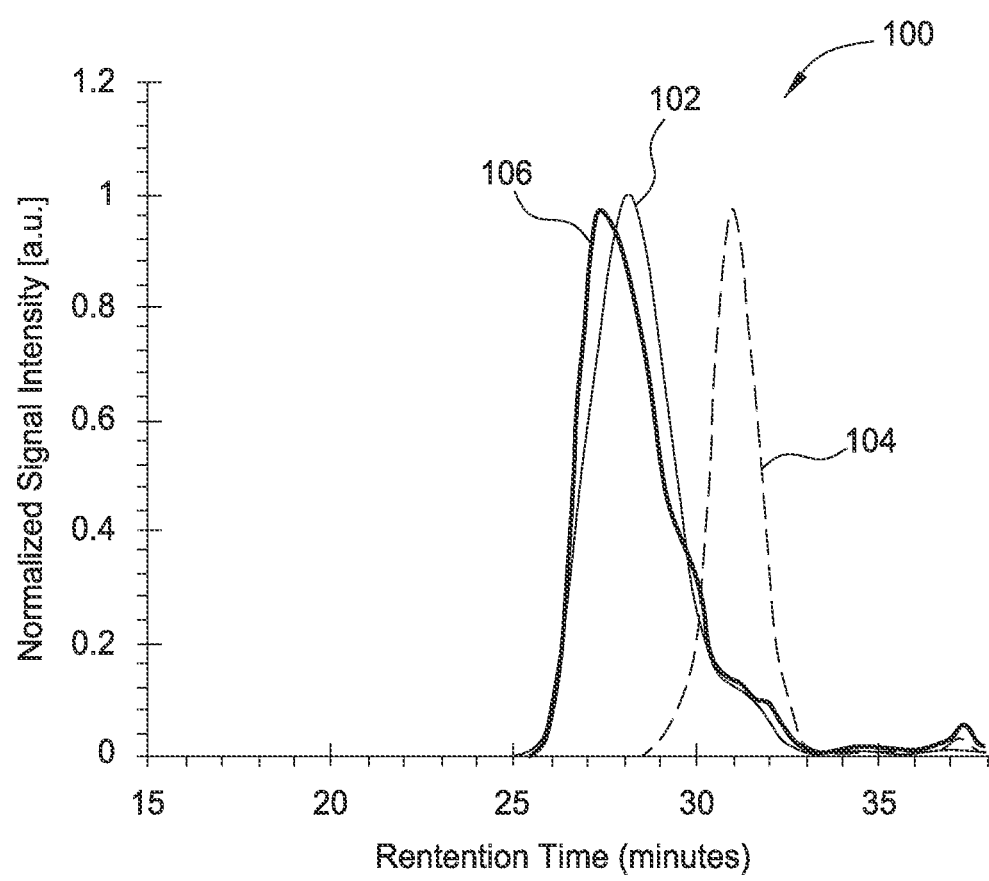
FIG. 1 is a graph showing a GPC analysis of a reaction according to one embodiment.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Similarly, the terms "further comprises," "may further comprise," and "further comprising," when used in this specification, specify the presence of additional features or components, without precluding the presence or addition of other features or components. The terms "further comprises," "may further comprise", and "further comprising" in this specification do not mean that any features or components are excluded from any embodiments. When a range is used to express a possible value using two numerical limits a and b (e.g., a concentration of a ppm to b ppm), unless otherwise stated the value can be a, b, or any number between a and b.

Chemical structures are presented herein using the following general notation:

$$[\text{structure}]_n$$

This notation is intended to define a repeated chemical structure within a larger structure, or molecule. Use of brackets around a chemical structure, with a letter subscript "n" generally indicates that the structure is repeated "n" times. Letters other than "n" may be used, and in each case, the letter subscript stands for a positive integer of at least 3. Unless otherwise noted, there is no theoretical upper limit to the value of the subscript. The notation is intended to refer to all possible polymers, of any feasible size, having the structure. However, kinetic and thermodynamic circumstances of individual chemical reactions, such as viscosity, temperature, and monomer availability may limit the growth of polymers in specific cases.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

The inventors have discovered new polymers that include a plurality of N-J-N or N—C—S repeating units, wherein each J is independently a carbon atom, an alkyl group, or an aryl group; a plurality of hydrophilic groups bonded with the repeating units; and a plurality of hydrophobic groups bonded with the hydrophilic groups and the repeating units. Such polymers can be made into hydrogels by exposure to water, and the resulting hydrogels can be used as delivery vehicles for theranostic components. The hydrogels can be physical hydrogels or chemical hydrogels. A physical hydrogel is a polymer that absorbs water to become a gel denominated primarily by non-covalent linkages between polymer chains. A chemical hydrogel is a covalently cross-linked polymer that absorbs water to become a gel.

The polymers are made by chemical synthesis of compositions involving hexahydrotriazine adducts or polythioaminal (PTA) adducts. Thus, the polymers may have a portion that is a hexahydrotriazine adduct and/or a portion that is a PTA adduct. The compositions may involve hexahydrotriazine crosslinks or thioaminal polymers with hydrophobic and hydrophilic segments. One class of polymers includes hexahydrotriazine crosslinks with polyethylene glycol ("PEG") spacers. Another class involves thioaminal polymers with hydrophobic linkers.

The hexahydrotriazine based compositions are characterized by hexahydrotriazine centers linked by spacers having hydrophilic and hydrophobic components. Thus, for example, some such compositions will have the general structure

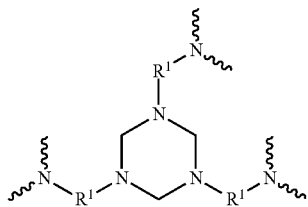

(1)

where $R^1$ is a hydrophilic segment. Because $R^1$ is hydrophilic, and because the polymer network of structure (1) is cross-linked, polymers having this structure will absorb water to become a chemical hydrogel. An example is as follows:

In reaction [1], a diamine participates in a Michael addition reaction with a hexahydrotriazine substituted with olefinic substituents, in this case an acryloyl group, at each nitrogen atom of the triazine ring (1,3,5-triacryloylhexahydro-1,3,5 triazine, CAS #959-52-4, commercially available from Sigma-Aldrich). The diamine in this case is a PEG diamine, which imparts a hydrophilic segment to the resulting polymer. Thus, for this example, $R^1$ is is a PEG polymer. In an exemplary reaction, the PEG diamine has a number-average molecular weight ($M_n$) of about 4-8 kiloDaltons (kDa), with specific reactions having been performed using PEG diamines at $M_n$ values of 4.6 kDa, 6.0 kDa, and 8.0 kDa. The reactions were performed in a solution that was 90 wt % water. The resulting polymers formed hydrogels that were not observed to decay, degrade, or decompose for weeks.

In reaction [1] any primary diamine, linear, branched, cyclic, and/or aromatic, with or without hetero-atoms such as oxygen, sulfur, and nitrogen at locations other than the primary amine groups, may be used to make a polymer according to structure (1). If the diamine has a hydrophilic core, such as PEG, polylactone, polyoxazoline, or polycaprolactone, and the triazine linking groups are hydrophobic, the resulting polymer will absorb water to make a hydrogel. If the diamine has a hydrophobic core (i.e. $R^1$ is hydrophobic), such as a hydrocarbon core, the diamine can be dissolved in an organic solvent that also dissolves PEG, such as an aromatic hydrocarbon solvent, alcohol, ketone, glycol ether, ester, or chloroform. The diamine can then be

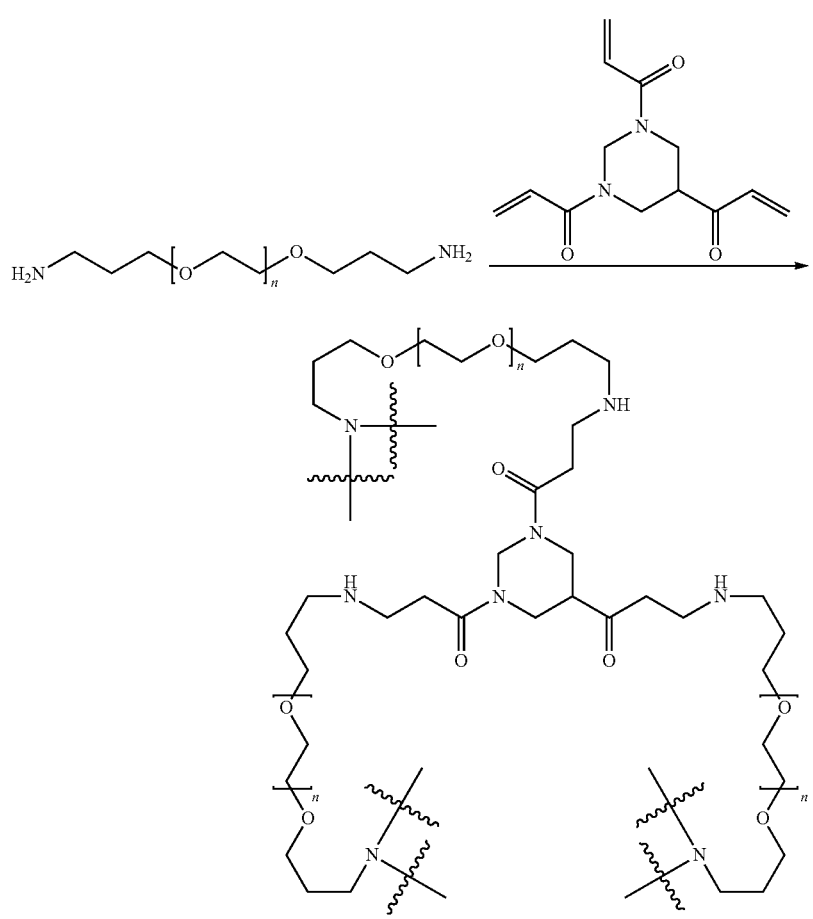

[1]

copolymerized with PEG or another hydrophilic moiety (with appropriately selected solvent), and amine terminated to form a block hydrophobic-hydrophilic diamine precursor to react with an olefin-functionalized triazine in reaction [1]. The diamine precursor may be isolated prior to reacting with the triazine, if desired, and depending on the particular solubility properties of the diamine, the reaction may be performed in water, as described above, or another protic solvent. Thus, in structure (1), $R^1$ includes hydrophilic portions, and may include hydrophobic portions as well.

It should be noted that the triazine substituents need not be the same, as they are shown in reaction [1]. In fact, they need not all be reactive under Michael addition. If at least one substituent is a Michael addition acceptor, a hydrogel forming polymer will result under the conditions otherwise described herein. It should also be noted that a mixture of different triazine and diamine precursors may be used to make a hydrogel forming multi-polymer according to reaction [1]. Reaction [1] may be performed in a solvent such as water, or another aqueous solvent, and is typically performed at room temperature or with slight heating to, for example, 50-80° C. Viscosity of the mixture may be managed to grow polymers of any desired average molecular weight using reaction [1] by using more or less solvent, and the polymer may be recovered as a solid by drying the viscous mixture.

Reaction [1] is a way to make a hydrogel forming polymer with N-J-N repeating units, where J is an alkyl group. The hydrogels available via reaction [1] are generally chemical hydrogels.

Another class of hydrogel forming polymers use various thioaminal polymers with N—C—S repeating units. Such polymers may have either of the following structures:

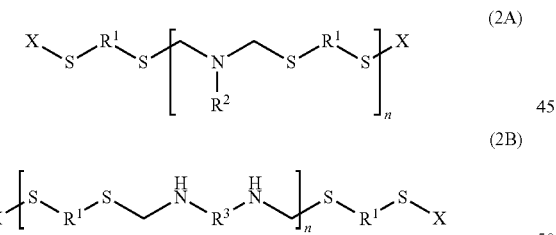

wherein each instance of $R^2$ is an organic or hetero-organic group and each instance of $R^3$ is an electron-deficient organic or hetero-organic group, and each instance of X is independently a hydrophobic group. Structure (2A) is a PTA with an S—C—N—C—S type repeating linkage, while structure (2B) is a PTA with an S—C—N—$R^3$—N—C—S type repeating linkage. $R^3$ may be an aryl or alkyl group in some embodiments. In other embodiments, $R^3$ may be $C_aF_b$, where a and b are integers; $NO_2$; $C_6H_4Q$, where Q is Br, Cl, $NO_2$, $CF_3$, F, $CO_2CH_3$, $CO_2H$, or CN; or a heterocycle. $R^1$ may be aryl, alkyl, PEG, polyester, or polyamide in some embodiments. In one example, $R^1$ is hexyl. Hydrophobic X groups useful for certain embodiments may contain, and may be derived from precursors selected from the group consisting of,

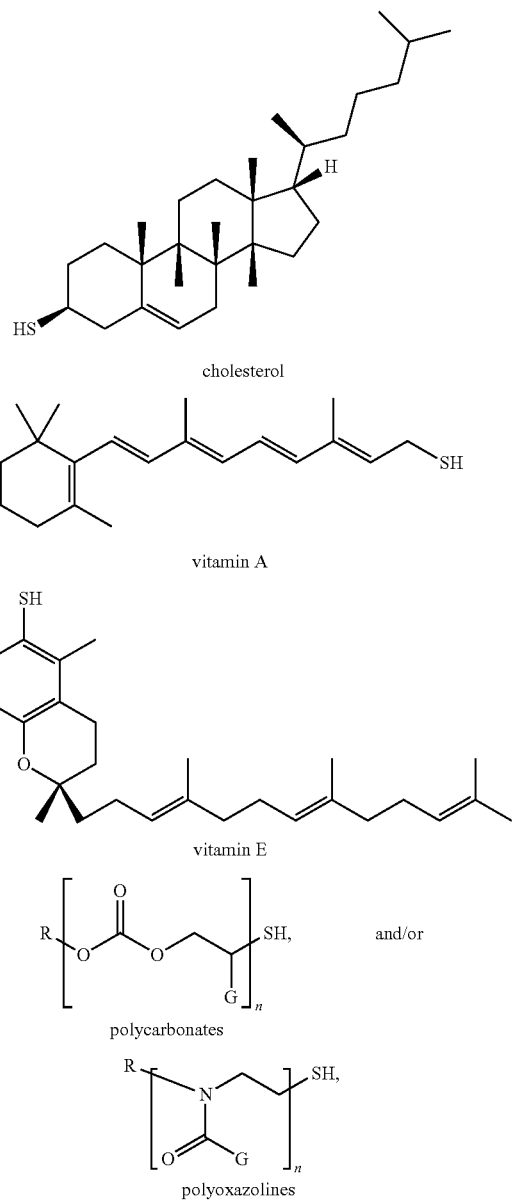

where G is any carbon-bondable substituent. Each of the foregoing structures is thio-terminated to bond with the thiol end-group of a PTA to form structure (2A) or (2B).

The structures (2A) may be made by reacting a hexahydrotriazine having the general structure

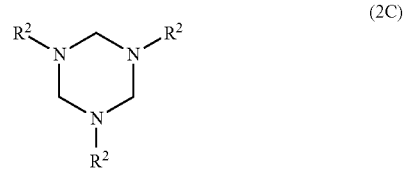

with a diamine of general structure HS—$R^1$—SH to form a PTA having general structure

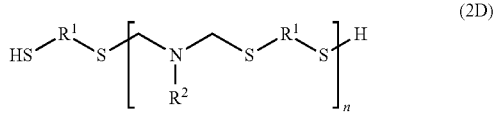

(2D)

characterized by repeated S—C—N—C—S linkages, and then attaching hydrophobic groups to the PTA, as follows:

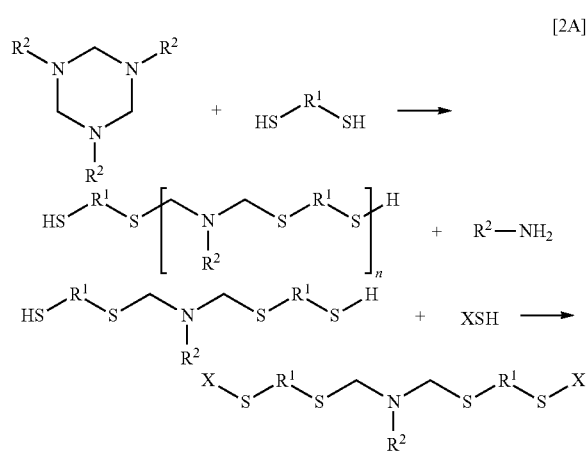

[2A]

Either or both reactions of the reaction scheme [2A] may be performed in a polar aprotic solvent, such as N-methyl pyrrolidone (NMP) or dimethylformamide (DMF), at a temperature from room temperature up to about 150° C. Byproduct amines $R^2NH_2$ from the ring-opening of the hexahydrotriazine may be remove by volatilizing, if the byproducts are volatile, or by including an amine scavenger orthogonal to the other species of the reaction, such as a cyclic carbonate or anhydride. The polymer (2D) may be recovered from the first reaction mixture by evaporating solvent and unreacted monomers, optionally under vacuum, and then redissolved in a solvent for addition of the hydrophobic X groups. As noted in reaction scheme [2A] and described above, the hydrophobic X groups may be added as a thiol precursor, which will react with the intermediate PTA polymer to form thioether bonds at either end of the molecule.

The structures (2B) may be formed by reacting a diamine having general structure $H_2N—R^3—NH_2$ with the dithiol described above and paraformaldehyde in a reaction scheme that includes formation of an imine intermediate, as follows:

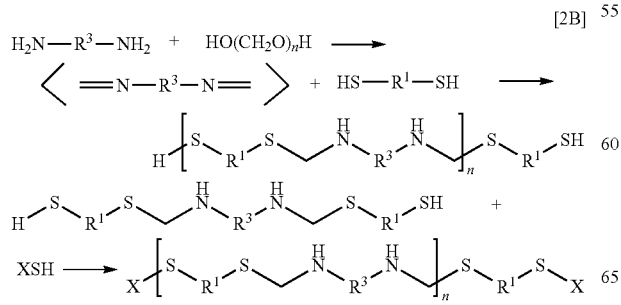

[2B]

The reaction scheme [2B] may be performed in solvents such as NMP and DMF, or in bulk, at temperatures from room temperature up to 150° C., for example at 80-85° C. It is believed that the electron-deficient diamine reacts with paraformaldehyde to form the stable imine intermediate 〈=N—R³—N=〉, which in turn reacts with the dithiol to form a PTA intermediate polymer. The PTA intermediate polymer has the general structure

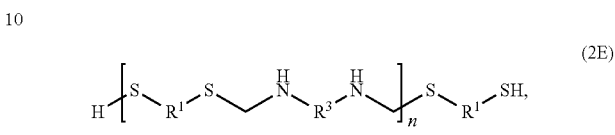

(2E)

characterized by repeated S—C—N—R³—N—C—S linkages. As above, the hydrophobic X groups may be added by recovering the PTA polymer, redissolving in a solvent, and adding a thiol precursor of the hydrophobic X group to form thioether bonds. In some embodiments, R³ includes an aromatic structure. The structures (2A) and (2B) may be triblock polymers with sections having opposite affinity for water. As noted above, the X groups may be hydrophobic. Where R¹ is hydrophilic, such as a PEG polymer, and the X groups are hydrophobic, the resulting polymer (2B) will absorb water to produce a physical hydrogel.

The X groups may include aromatic components. For example, a polymer of structure (2A) may be reacted with a thiol reactive aromatic species having the structure

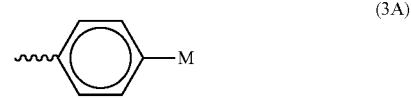

(3A)

where M is OH, $NH_2$, or COOH. The hydrogel forming polymer thus has the structure

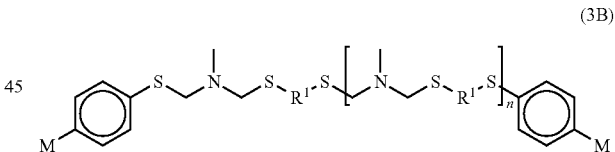

(3B)

where structure (3B) is like structure (2A) wherein R³ is a methyl group. Polymers having structure (3B) may be made by reacting the PTA of reaction [2A] or [2B] (formed from 1,3,5-trimethylhexahydrotriazine) above with a thiobenzyl compound having the structure

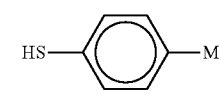

in the presence of an alkylating agent such as $CHCl_3$.

The X groups may themselves be polymers. In one example, a PEG PTA of structure (2A) may be reacted with a thiol terminated polycarbonate to form a hydrogel forming triblock polymer of structure (2B) with a hydrophilic PEG core and hydrophobic polycarbonate end groups, as follows:

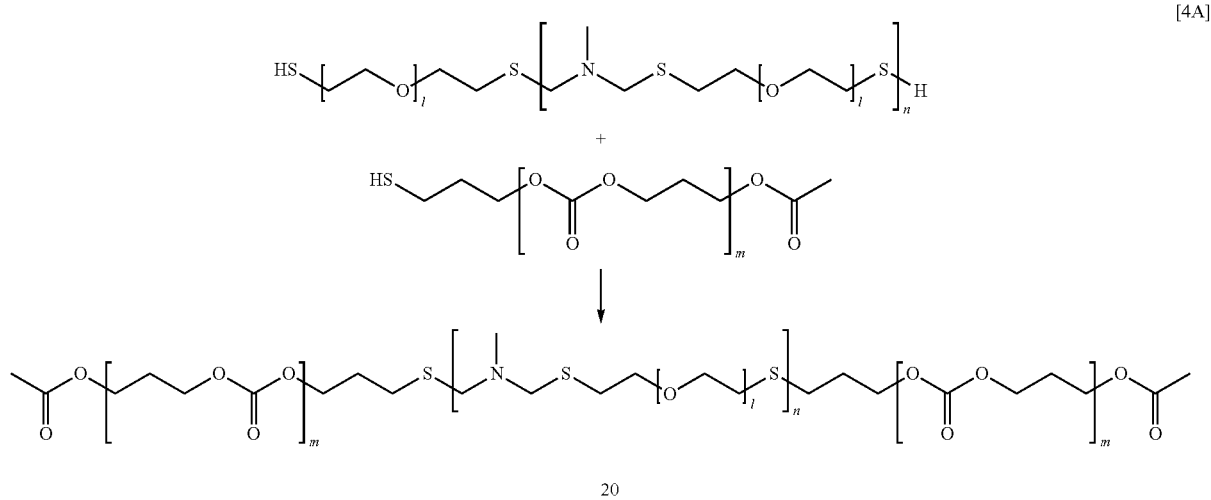

[4A]

FIG. 1 is a graph 100 showing a GPC analysis of reaction [4A]. Three plots 102, 104, and 106 are shown in the graph 100 on a normalized scale. Plot 102 is a GPC of the PEG PTA, plot 104 is of the thiol terminated polycarbonate, and plot 106 is of the product. The product is a triblock polymer with a single molecular weight mode at lower retention time than either the PEG or polycarbonate precursor, indicating higher molecular weight and single molecular weight distribution.

In another example, hydrophilic X groups may be added to a hydrophobic PTA. In one example, an alkyl PTA reacts with a dithioerithritol PTA, as follows:

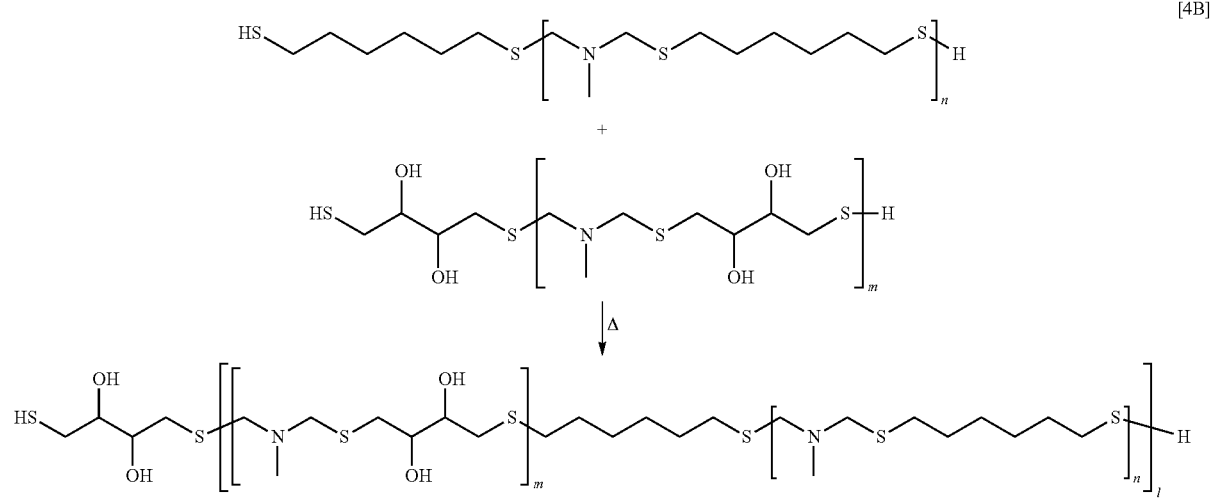

[4B]

Figure 2:
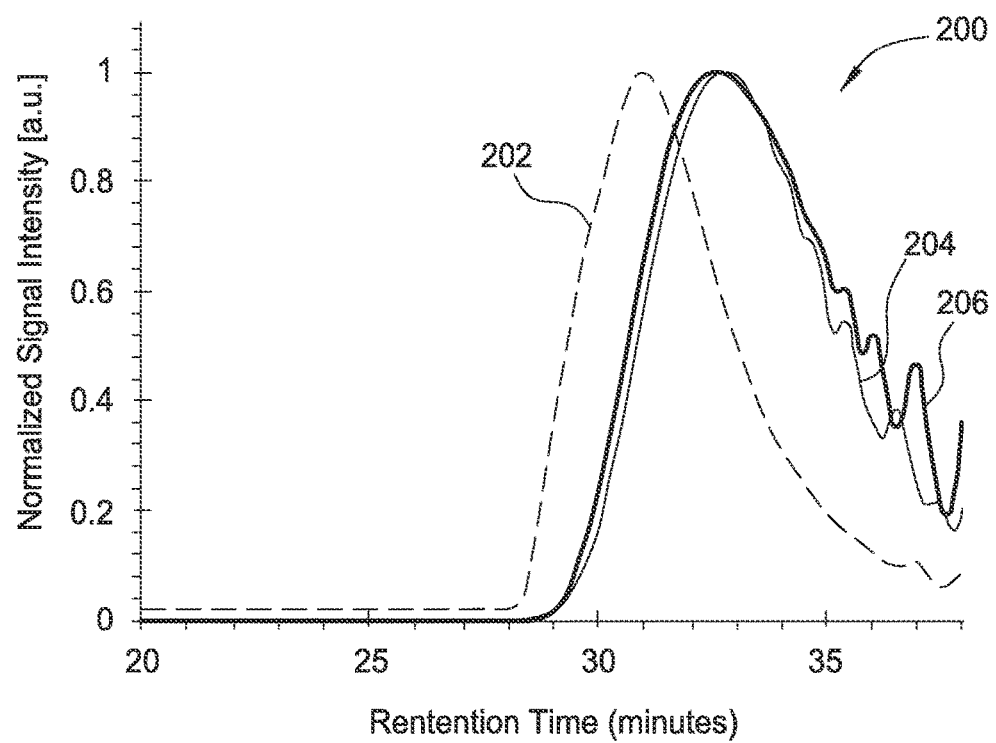
FIG. 2 is a graph showing a GPC analysis of a reaction according to another embodiment.

FIG. 2 is a graph 200 showing a GPC analysis of reaction [4B]. Three plots 202, 204, and 206 are shown in the graph 200 on a normalized scale. Plot 202 is a GPC of the dithioerithritol PTA, plot 204 is of the alkyl PTA, and plot 206 is of the product. Note that the product exhibits a single peak with retention time between that of the two precursor materials. In general, reaction [4B] may be performed using the alkyl PTA of structure (2D) above with dithioerythritol to form a polymer having the general structure

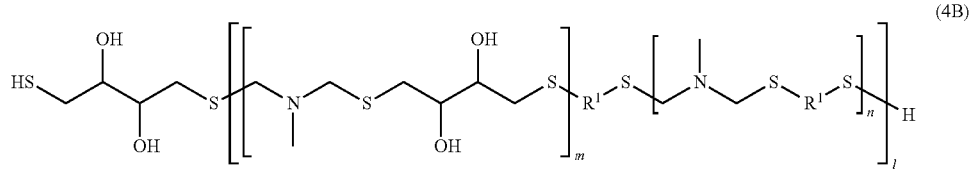

(4B)

wherein $R^1$ is defined above. The exemplary reactions above may be performed in chloroform at a temperature of 40-150° C. at a duration up to about 4 hours.

Another network polymer that can become a chemical hydrogel is a cross-linked polymer having the general structure

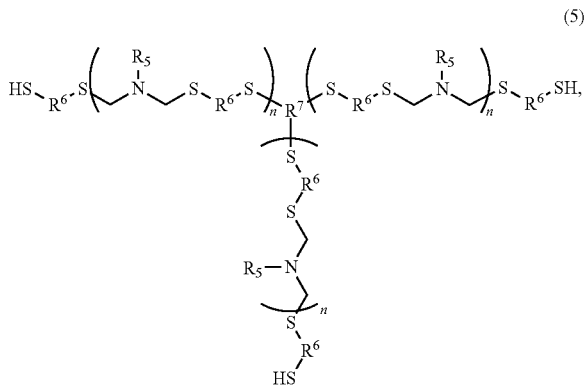

(5)

where $R^7$ is trivalent group that may be hydrophilic or hydrophobic, may be formed by reacting a PTA with a trithiol $R^7(SH)_3$. If $R^6$ is hydrophilic, such as a PEG, or PEG containing, polymer or oligomer, the polymer of structure (5) will absorb water to form a chemical hydrogel. In some examples, $R^6$ and $R^7$ can both be hydrophilic, and the resulting polymer will form a chemical hydrogel. In general, for polymers of structure (5) that form hydrogels, the degree of water uptake by such polymers will depend on density of crosslinking of the polymer. For example, low crosslink density such as 5 mol %, where crosslink density is here defined as $M_c/M_n$, where $M_c$ is the number-average molecular weight of molecular chains between crosslinks and $M_n$ is the overall number-average molecular weight of the overall polymer, can result in water uptake up to 90 wt %. Crosslink density may be influenced by molecular weight of the segments used to assemble the structure (5).

The PTA used to form the structure (5) is the polymer of structure (2D) described above. The polymer of structure (5) may also be alkylated and/or functionalized with X groups, as described above. It should be noted that structure (5) has three branches, but the structure could have more than three branches While the foregoing is directed to embodiments of the present invention, other and further embodiments of the invention may be devised without departing from the basic scope thereof, and the scope thereof is determined by the claims that follow.

What is claimed is:

1. A polymer, comprising:
   a plurality of N-J-N repeating units, wherein each J is independently a carbon atom, an alkyl group, or an aryl group;
   a plurality of hydrophilic groups bonded with the repeating units; and
   a plurality of hydrophobic groups bonded with the hydrophilic groups and the repeating units, all in the general structure

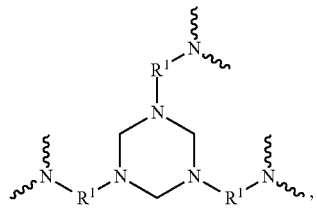

wherein each instance of $R^1$ includes an acryloyl group, a lactone group, or a caprolactone group.

2. The polymer of claim 1, wherein each instance of X is independently selected from the group consisting of a cholesterol, a polycarbonate, a polyoxazoline, a vitamin A, and a vitamin E.

3. A hydrogel formed by exposing the polymer of claim 1 to water.

4. A theranostic delivery matrix comprising the hydrogel of claim 3.

* * * * *